(12) United States Patent
Nassif et al.

(10) Patent No.: US 8,859,008 B2
(45) Date of Patent: Oct. 14, 2014

(54) BONE SUBSTITUTE AND METHOD FOR THE PREPARATION THEREOF

(75) Inventors: Nadine Nassif, Paris (FR); Frédéric Gobeaux, Paris (FR); Marie-Madeleine Giraud Guille, Paris (FR); Gervaise Mosser, Paris (FR)

(73) Assignees: Universite Pierre et Marie Curie, Paris (FR); Centre National de la Recherche Scientifique, Paris (FR); Ecole Pratique des Hautes Etudes, Paris (FR)

( * ) Notice: Subject to any disclaimer, the term of this patent is extended or adjusted under 35 U.S.C. 154(b) by 624 days.

(21) Appl. No.: 12/999,507

(22) PCT Filed: Jun. 26, 2009

(86) PCT No.: PCT/FR2009/051233
§ 371 (c)(1),
(2), (4) Date: Jun. 27, 2011

(87) PCT Pub. No.: WO2010/004182
PCT Pub. Date: Jan. 14, 2010

(65) Prior Publication Data
US 2011/0250289 A1 Oct. 13, 2011
US 2012/0076870 A9 Mar. 29, 2012

(30) Foreign Application Priority Data
Jun. 30, 2008 (FR) ...................................... 08 03663

(51) Int. Cl.
*A61K 33/42* (2006.01)
*A61P 19/08* (2006.01)
*A61L 27/46* (2006.01)

(52) U.S. Cl.
CPC ....................................... *A61L 27/46* (2013.01)
USPC ......................................................... 424/601

(58) Field of Classification Search
None
See application file for complete search history.

(56) References Cited

PUBLICATIONS

Venugopal, J.; Low, S.; Choon, A. T.; Kumar, T. S. S.; Ramakrishna, S. Mineralization of osteoblasts with electrospun collagen/hydroxyapatite nanofibers. J. Mater. Sci. 2008, 19, 2039-2046 (available online Oct. 24, 2007).*

(Continued)

*Primary Examiner* — Mina Haghighatian
*Assistant Examiner* — Erin Hirt
(74) *Attorney, Agent, or Firm* — Sofer & Haroun, LLP

(57) ABSTRACT

The invention relates to a material that can be used as a bone substitute and to a method for the preparation thereof. The material comprises an organic phase (I) comprising striated collagen fibrils constituted of collagen I triple helices, said fibrils being organized over a large distance according to a 3D geometry associating aligned domains and cholesteric domains, and also isotropic domains where they are not organized; and a mineral phase (II) comprising apatite crystals having a hexagonal crystalline structure, space group 6/m, comprising at least calcium ions and phosphate ions; the axis c of said apatite crystals of the mineral phase is coaligned with the longitudinal axis of the striated collagen fibrils of the organic phase and the collagen content in the material is at least 75 mg/cm$^3$. The method for preparing the material comprises preparing an initial acidic aqueous solution of collagen which is a precursor for the organic phase (I), and at least one aqueous solution of precursors for the mineral phase (II) and precipitating the collagen by increasing the pH to a value of at least 7. According to this method: the concentration of collagen in the acidic aqueous solution is at least 75 mg/ml and remains constant during said increase in pH; the mineral phase precursors comprise at least one calcium salt and at least one phosphate salt; the precipitation of the mineral phase (II) is carried out by bringing the mineral phase precursor solution into contact with the organic phase (I), said bringing into contact being carried out before or after the precipitation of said organic phase (I).

7 Claims, 4 Drawing Sheets a b

(56) References Cited

PUBLICATIONS

Sachlos, E.; Gotora, D.; Czernuszka, J. T. "Collagen Scaffolds Reinforced with Biomimetic Composite Nano-sized Carbonate substituted hydroxyapatite crystals and Shaped by Rapid Prototyping to Contain internal microchannels." Tissue Engineering, 2006, v. 12, No. 9, 2479-2487.*

Tampieri, A.; Sandri, M.; Landi, E.; Pressato, D; Francioni, S.; Quarto, R.; Martin, I. "Design of graded biomimetic osteochondral composite scaffolds." Biomaterials, 2008, v. 29, p. 3539-3546.*

Olstza, M. J. et al. "Bone structure and formation: A new perspective." Materials Science and Engineering: R: Reports, vol. 58, Issues 3-5, Nov. 28, 2007, pp. 77-116.*

APS Fibrous Connective Tissue sheet; http://www.aps.uoguelph.ca/~swatland/ch2_3.htm; Archived by wayback machine May 2000.*

* cited by examiner

BONE SUBSTITUTE AND METHOD FOR THE PREPARATION THEREOF

RELATED APPLICATIONS

This application is a National Phase application of PCT/FR2009/051233, filed on Jun. 26, 2009, which in turn claims the benefit of priority from French Patent Application No. 08 03663, filed on Jun. 30, 2008, the entirety of which are incorporated herein by reference.

BACKGROUND

1. Field of the Invention

The present invention relates to a bone substitute and to a method for the preparation thereof.

2. Description of Related Art

Bone is a hybrid material constituted mainly of cells, collagen type I which constitutes an organic protein network, and a mineral phase consisting of hydroxyapatite crystals of nanometric size. This large-scale organic/mineral association in three dimensions gives the bone tissue both elasticity and hardness, allowing it to withstand the forces which are applied thereto. Bone is therefore hard, dense and very strong.

Weiner & Wagner (Ann. Rev. Mater. Sci. 28, 271-298, 1998) have proposed a description of a hierarchical organization on various scales which can be broken down into seven levels described as follows and which are illustrated by the appended FIG. 1:

- level 1 (FIG. 1a): the two major constituent basic components of bone, i.e. the hydroxyapatite platelets and the striated collagen fibrils, constitute the first hierarchical level of organization. This is the lowest level of organization, on the nanometric scale. The apatite phase is in particular characterized by the presence of characteristic inter-reticular planes such as (002) and (300). The apatite crystals, at this level of organization, do not have a particular orientation. The collagen fibrils are characterized by a periodic striation, which is visible by electron microscopy, and which results from the assembly of the collagen I molecules, inducing a periodic shift of 67 nm;
- level 2 (FIG. 1b): the coalignment of the hydroxyapatite platelets according to their axis c, along the main axis of the striated collagen fibrils, constitutes the second level, i.e. the inter-reticular planes (002) of the apatite are oriented perpendicular to the main axis of the fibrils and, therefore, according to the axial periodicity (i.e. according to the striations) of the collagen fibrils (striation=67 nm). The term mineralized collagen fibrils is used (width 100 to 300 nanometers). Level 2 is also on the nanometric scale;
- level 3 (FIG. 1c): several mineralized collagen fibrils are assembled side by side in parallel bundles, forming a mineralized collagen fiber (width 1 to 3 micrometers). The micrometric scale is reached at organization level 3;
- level 4 (FIG. 1d): it is complex since the mineralized collagen fibrils or fibers can organize in three dimensions. Specifically, at this level, it is possible to distinguish the coexistence of domains where the fibrils/fibers are aligned in a preferential direction over a large distance and/or form arched structures characteristic of their stack according to a "cholesteric" geometry. Domains where the fibrils/fibers do not organize ("isotropic" domains) are also distinguished. The scale varies from micrometric to millimetric;
- level 5 (FIG. 1e): the compact bone has an arrangement of parallel cylindrical structures of millimetric size, denoted "osteons". In section, these osteons appear to consist of concentric collagen lamellae;
- level 6 (FIG. 1f): the cell-rich central part of the long bones is called "spongy bone". In this bone, bone lamellae form a macroporous network of thin and irregular rows. The compact bone/spongy bone combination constitutes organization level 6. The scale is more than one millimeter;
- level 7 (FIG. 1g): the final level is quite simply the whole bone.

Several classes of synthetic materials (denoted "implant materials") or is natural materials (denoted "grafts") are proposed in the prior art. Implant materials are generally bioinert, i.e. simply tolerated by the organism, or biocompatible, i.e. they integrate perfectly into the host organism. A graft is a bone tissue taken from the person for whom it is intended (autograft) or from a third person (allograft), and it is generally osteoconductive, i.e. it is capable of guiding bone regrowth.

An osteoinductive bone substitute, i.e. one which is capable of inducing bone reconstruction, nevertheless constitutes an ideal substitute. The development of such a material is complex. Putting into place such a material requires the use of constituents which have a specific crystalline phase and chemical nature in order to optimize perfect integration thereof in a human or animal body, and to thus avoid rejection. Its three-dimensional organization must be reconstituted in order to provide, firstly, the mechanical properties and, secondly, a porosity suitable for the colonization of said substitute by the host tissue. The access to the organization of the organic bone network (20% by mass), and also the association thereof with the mineral phase (70% by mass) in the tissue are very difficult to reproduce in vitro.

Many studies have been carried out with a view to synthesizing bone substitutes, and in particular studies relating to collagen mineralization. The mineralization of turkey bone tendon collagen has been studied by W. Traub et al. [Proc. Natl. Acad. Sci. USA 1989, 86, 9822-9826], but the material obtained does not display an organization analogous to that of bone. Other tests have been carried out with purified collagen in vitro, but the conditions of strong dilution under which the tests were carried out did not make it possible to obtain a material having the bone density and the three-dimensional collagen organization that are found in living bone tissues [cf. D. Lickorish el al. (J. Biomed. Mat. Res. 2004, 68A, 19-27); S. Yunoki et al. (Mat. Lett., 2006, 60, 999-1002); D. A. Wahl et al. (Eur. Cell. Mat. 5 2006, 11, 43-56)].

The crystallization of calcite $CaCO_3$ from a solution of $CaCl_2$ under an ammonia atmosphere generated by the thermal decomposition at ambient temperature of a powder of $(NH_4)CO_3$ has been described by L. Addadi et al. (Proc. Natl. Acad. Sci. USA 1987, 84, 2732-2736).

It is also known practice to precipitate collagen from an acid solution by increasing the pH. R. L. Ehrman et al. (J. Nat. Cancer Inst. 1956, 16, 1375-1403) describe a method in which a solution of collagen in acetic acid is brought into contact with $NH_3$ vapors. It transforms into a gel containing fine grains. The structure of the material obtained is not described.

M. M. Giraud-Guille et al. (J. Mol. Biol. 1995, 251, 197-202) and (J. Mol. Biol. 1992, 224, 861-873) describe the "liquid crystal" structure obtained using a concentrated solution of collagen and also the sol-gel transition obtained by raising the pH from acidic to basic.

G. Mosser, M. M. Giraud-Guille el al. (Matrix Biol. 2006, 25, 3-13) 20 describe a method in which an acidic solution of collagen (5 mg/mL) is gradually concentrated in glass microchambers in order to obtain a far-reaching helicoidal organization of the collagen molecules and also a concentration gradient. The solution is then brought into contact with ammonia vapors, in order to form collagen fibrils and to stabilize the organization put in place in the liquid phase.

B. A. Harley et al. (Biomaterials 2006, 27, 866-874) describe the production of a structured matrix of collagen also containing a glucosaminoglycan. Collagen microfibrils are homogeneously mixed with chondroitin sulfate at 4° C. The solution is then centrifuged in a mold, ultra-rapidly frozen, freeze-dried, and then crosslinked at 105° C. under a vacuum of 50 mTorr for 24 hours. The fibrillar nature of the collagen is not described.

C. Guo el al. (Biomaterials 2007, 28, 1105-1114) describe the use of magnetic beads for aligning a solution of collagen fibrils. A collagen solution prepared in a phosphate buffer at concentrations of 2.5 mg/ml, maintained at 4° C., is brought into contact with the magnetic beads. The same samples are also prepared in the presence of cells at a final collagen concentration of 1.2 mg/ml. In both cases, the samples are placed in a magnetic field of less than 1G during the induction of fibrillogenesis produced by an increase in temperature to 37° C. A $CO_2$ atmosphere is also used when cells are integrated into the matrix. The matrices are very loose and the fibrillar nature of the collagen is not mentioned. M. J. Olsza el al. (Calcif. Tissue Int. 2003, 72, 583-591) describe the calcification of a collagen sponge in the presence or absence of a polymer of the poly(aspartic acid) type. The collagen sponge is constituted of collagen type I obtained from bovine tendon. The mineral is calcium carbonate and not calcium phosphate, no apatite phase is therefore obtained. The presence of striated fibers is not demonstrated and the in collagen fibers are not oriented. J. H. Bradt et al. (Chem. Mater. 1999, 11, 2694-2701) describe a method in which two solutions are prepared at 4° C., the first being a solution of collagen (calf dermis collagen type I) at 1 mg/mL acidified with HCl and containing $CaCl_2$, and the second being a buffer solution containing phosphate ions. The phosphate solution is then mixed with the collagen solution, making it is possible to achieve a pH of 6.8, and the whole mixture is heated to 30° C. Coprecipitation gives a mixture of phases containing calcium phosphate, hydroxyapatite and octacalcium phosphate. In addition, the collagen fibers are isolated nonoriented fibers and do not constitute a dense matrix. N. Gehrke, N. Nassif et al. (Chem. Mater. 2005, 17, 6514-6516) describe the remineralization, with calcium carbonate, in the presence or absence of a polymer of the poly(aspartic acid) type, of the organic network of previously demineralized mother-of-pearl.

OBJECTS AND SUMMARY

None of the synthesis methods known to date makes it possible to obtain a bone substitute which reproduces level 4 of three-dimensional organization of collagen associated with a mineral phase of apatite crystals which is observed in natural bone.

The objective of the present invention is to provide a synthetic material which can be used as a biocompatible bone substitute having a structure very close to the structure of living bone (level 4), and also a method for preparation thereof.

The synthetic material according to the present invention comprises an organic phase (I) and a mineral phase (II).

The organic phase (I) comprises striated collagen fibrils constituted of collagen I triple helices and in which the periodicity of the striations is approximately 67 nm, said fibrils being organized over a large distance according to a 3D geometry associating aligned domains and cholesteric domains, and also isotropic domains where they are not organized.

The mineral phase (II) comprises apatite crystals having a hexagonal crystalline structure, space group 6/m, said crystals comprising at least calcium ions and at least phosphate ions.

In the material in accordance with the invention, the axis c of the apatite crystals of the mineral phase is coaligned with the longitudinal axis of the striated collagen fibrils of the organic phase.

The collagen content in said material is at least 75 mg/cm³.

In said material, the order of magnitude of the various domains (cholesteric, alignment, isotropic) is about fifty microns approximately.

According to one particular embodiment, the mineral phase consists of pure hydroxyapatite crystals. For the purpose of the present invention, the term "pure hydroxyapatite" is intended to mean a hydroxyapatite free of other crystalline phosphate phases, such as brushite.

In one particular embodiment of the invention, the mineral phase consists of crystals of stoichiometric hydroxyapatite of formula (I) below:

$$Ca_{10}(PO_4)_6(OH)_2 \qquad (I)$$

According to one particular embodiment of the invention, the Ca/P atomic ratio of the crystals of hydroxyapatite of formula (I) is 1.67.

According to another embodiment of the invention, the mineral phase comprises apatite crystals also comprising at least hydroxide ions and in which the phosphate ions (type B) and/or the hydroxide ions (type A) are partially replaced with carbonate ions.

In these hydroxyapatites, one or more sites of the crystalline structure can be ion-free. In this case, they are nonstoichiometric hydroxyapatites comprising what is then referred to as one or more ion gaps.

In another embodiment, the mineral phase comprises crystals of apatite comprising $Ca^{2+}$ ions, $PO_4^{3-}$ ions and OFF ions, and in which at least one of the $Ca^{2+}$, $PO_4^{3-}$ or OFF ions is partially replaced with other ions.

Among the ions capable of partially replacing the $Ca^{2+}$ ions, mention may be made of $Mg^{2+}$, $Cu^{2+}$, $Sr^{2+}$, $Ba^{2+}$, $Zn^{2+}$, $Cd^{2+}$, $Pb^{2+}$, $Na^+$, $K^+$ and $Eu^{3+}$ ions.

Among the ions capable of partially replacing the $PO_4^{3-}$ ions, mention may be made of $CO_3^{2-}$, $SiO_4^{3-}$, $AsO_4^{3-}$, $MnO_4^{3-}$, $VO_4^{3-}$, $CrO_4^{3-}$ and $HPO_4^{2-}$ ions.

Among the ions capable of partially replacing the $OH^-$ ions, mention may be made of $CO_3^{2-}$, $F^-$, $Cl^-$, $Br^-$, $I^-$, $S^{2-}$ and $O^{2-}$ ions.

The material according to the invention may also contain a minute amount of proteoglycans, of glycosaminoglycans and/or of organic molecules which promote mineralization. The term "minute amount" is intended to mean a proportion of less than 2%.

The characteristics of a material of the invention can be determined by optical microscopy analyses, scanning electron microscopy SEM analyses, transmission electron microscopy TEM analyses and X-ray diffraction analyses.

Semi-thin sections of a material according to the invention, observed by polarized-light optical microscopy, show birefringence properties. In an ideal case, the observation of alternating illuminated bands and extinguished bands associated with the movement of these fringes during the rotation of the microscope platform indicates a helicoidal structure.

Samples of the material of the invention, analyzed by SEM, show oriented fibrils immerged in a mineralized layer, without individualized crystalline aggregates of about a micrometer.

Small-angle X-ray scattering images, taken on a material of the invention, show the anisotropic signal of the collagen fibrils and the harmonics of the period D=67 nm. Wide-angle X-ray scattering images show the main peaks of the apatite phase. The existence of a coalignment between the signal of the fibrils and that of the mineral characterizes the material of the invention. This coalignment is more particularly demonstrated locally in the zones where the fibrils are aligned.

A material according to the invention can be obtained by means of a method which consists in preparing an initial acidic aqueous solution of collagen which is a precursor for the organic phase (I), and at least one aqueous solution of precursors for the mineral phase (II), and in precipitating the collagen by increasing the pH to a value of at least 7. It is characterized in that:
- the concentration of collagen in the acidic aqueous solution is at least 75 mg/ml and remains constant during said increase in pH,
- the mineral phase precursors comprise at least one calcium salt and at least one phosphate salt,
- the precipitation of the mineral phase (II) is carried out by bringing the mineral phase precursor solution into contact with the organic phase (I), said bringing into contact being carried out before or after the precipitation of said organic phase (I). The duration of the contact is set according to the speed of precipitation and the level of mineral filler envisioned in the final material.

In a first embodiment of the method, the collagen of the organic phase (I) is precipitated before it is brought into contact with a neutral solution of precursors for the mineral phase (II). In this case, the solution of precursors for the mineral phase (II) contains at least said calcium salts and at least said phosphate salts. The proportion of mineral phase in the final material is modulated through the amount of ions introduced into the solution. In this embodiment, the collagen acquires its to fibrillar structure before it is brought into contact with the mineral phase.

In a second embodiment of the method, an acidic solution of precursors for the organic phase (I) is brought into contact with an acidic solution of precursors for (II). The mixture is then subjected to an increase in pH which induces coprecipitation of the collagen and of the apatite. In this embodiment, it is is particularly important to keep the initial concentration of collagen constant. A first means for avoiding dilution is to contain the concentrated acidic solution of precursors for the organic phase. (I) in a mold, the shape of which is suitable for the desired use and which is enclosed in a dialysis membrane. A second means is to introduce the concentrated collagen solution into a flexible envelope constituted of a dialysis membrane. The mold or said envelope is then immersed in the solution of precursors for the mineral phase (II).

When the mineral phase II of the material in accordance with the invention consists of crystals of pure hydroxyapatite, the method is preferably carried out in a closed chamber in which are placed:
- at least one first container containing an aqueous solution of at least one phosphate salt and of at least one calcium salt, which are precursors for the mineral phase II, in which solution at least one dialysis bag is immersed, said dialysis bag containing an initial acidic aqueous solution of collagen which is a precursor for the organic phase (I),
- at least one second container containing an aqueous ammonia solution or an $(NH_4)_2CO_3$ powder;

it being understood that:
- the (volume of mineral phase I precursor solution)/(closed chamber internal volume) ratio is approximately $2 \times 10^{-3}$,
- the height of the mineral phase 1 precursor solution contained in the first container ranges from 3 to 5 cm approximately, the diameter of said container being from 2 to 5 cm approximately;
- the (volume of aqueous ammonia solution)/(closed chamber internal volume) ratio is $8 \times 10^{-3}$ or the (volume of $(NH_4)_2CO_3$ powder)/(closed chamber internal volume) ratio is $6 \times 10^{-3}$ approximately.

When these conditions are adhered to, a material in which the mineral phase II consists of pure apatite, free of any other type of calcium phosphate phase, is obtained.

The initial acidic aqueous solution of collagen preferably has the following characteristics:
- its collagen concentration is between 75 mg/mL and 1000 mg/mL, preferably between 100 mg/mL and 400 mg/mL,
- its pH is less than 4, preferably less than 3, in the presence of acids, preferably 0.5 M acetic acid.

The solution of precursors for the mineral phase (II) preferably has the following characteristics:
- the concentration of calcium precursor, for example $CaCl_2$, is less than the solubility limit, preferably from 2.5 mM to 1.5 M, more particularly from 11 to 550 mM;
- the concentration of phosphate precursor, for example $NaH_2PO_4$, is less than the solubility limit, preferably from 1.5 to 900 mM, more particularly from 66 to 330 mM;
- the amounts of precursors are such that the Ca/P molar ratio is between 1.5 and 1.8, preferably about 1.67.

By way of example, the solubility limit at 20° C. is 7.08 M for $NaH_2PO_4$, and 3.83 M for $CaCl_2$.

When the mineral phase of the desired material comprises crystals of apatite comprising $Ca^{2+}$ ions, $PO_4^{3-}$ ions and $OH^-$ ions, and in which at least one of the $Ca^{2+}$, $PO_4^{3-}$ or $OH^-$ ions is partially replaced with other ions, the mineral phase precursor solution also contains one or more salts, the cation of which is intended to at least partially replace $Ca^{2+}$, and/or one or more salts, the anion of which is intended to at least partially replace $PO_4^{3-}$ and/or $OH^-$.

The salts of the cations intended to replace $Ca^{2+}$ are advantageously chosen from salts containing monovalent or divalent cations, for instance $MgCl_2$, $BaCl_2$, $SrCl_2$, NaCl, KCl and $NH_4Cl$. The $CO_3^{2-}$ precursor may be $NaHCO_3$. The amount of $CO_3^{2-}$ precursor is preferably such that the $NaH_2PO_4$/$NaHCO_3$ ratio is equal to 1. In the presence of carbonate, the Ca/(P+C) molar ratio is between 1.5 and 1.8, preferably about 1.67.

The mineral phase (II) precursor solution may also contain proteoglycans, glycosaminoglycans and/or organic molecules which promote mineralization, such as acidic amino acid polymer chains, preferably a poly(aspartic acid) having a chain length of between 5 and 150 amino acid units, preferably approximately 15, and with a concentration of between 0.01 µg/mL and 1.5 mg/mL, preferably 10 µg/mL.

The increase in the pH is advantageously carried out by means of a basic gaseous atmosphere, in particular an $NH_3$ atmosphere, or an $(NH_4)_2CO_3$ atmosphere in one particular embodiment in which $PO_4^{3-}$ or $OH^-$ is partially replaced with $CO_3^{2-}$.

In one particular embodiment, the method comprises an additional step during which the material obtained by coprecipitation is impregnated with an "SBF" ("Simulated Body Fluid") solution analogous to a biological fluid, and then the pH of the medium is adjusted to 7.4.

NaCl from 137 to 213 mM (for example, 213.0 mM)
NaHCO$_3$ from 1.2 to 6.3 mM (for example, 6.3 mM)
KCl from 3 to 4.5 mM (for example, 4.5 mM)
K$_2$HPO$_4$.3H$_2$O from 1 to 1.5 mM (for example, 1.5 mM)
CaCl$_2$ from 2.6 to 3.8 mM (for example, 3.8 mM)
Na$_2$SO$_3$Na$_2$SO$_4$ from 0.5 to 0.75 mM (for example, 0.75 mM)
MgCl$_2$.6H$_2$O from 1.5 to 2.3 mM (for example, 2.3 mM).

The concentrations of this SBF solution represent approximately 1.5 times those actually measured for a biological fluid (cf. Zhang L.-J. et al., Mater. Lett. 2004, 58, 719-722).

The pH can be adjusted to 7.4 with a mixture of tris(hydroxymethyl)aminomethane at 0.01 mol/L and HCl at 0.01 mol/L, at 37° C.

DETAILED DESCRIPTION

The present invention is described in greater detail by means of the following examples, to which it is not, however, limited.

In the examples, a collagen type I was used which was prepared from tails of young Wistar rats, according to the following procedure. The rat tail tendons are excised in a sterile laminar flow hood, and then washed in a phosphate buffered saline solution containing 137 mM of NaCl, 2.68 mM of KCl, 8.07 mM of Na$_2$HPO$_4$ and 1.47 mM of NaH$_2$PO$_4$, in order to remove the cells and the traces of blood. The tendons are then soaked in a 4M NaCl solution in order to remove the remaining intact cells and to precipitate a part of the high-molecular-weight proteins. After a further wash with the buffered saline solution, the tendons are dissolved in an aqueous solution containing 500 mM of acetic acid. The resulting solution is clarified by centrifugation at 41 000 g for 2 h. The proteins other than the collagen type I are selectively precipitated from a 300 mM aqueous NaCl solution, and then removed by centrifugation at 41 000 g for 3 h. The collagen is is recovered from the supernatant by precipitation from a 600 mM NaCl aqueous solution, followed by centrifugation at 3000 g for 45 min. The resulting pellets are dissolved in a 500 mM aqueous acetic acid solution, and then carefully dialyzed in the same solvent in order to completely remove the NaCl.

The solutions are kept at 4° C. and centrifuged at 41000 g for 4 h before being used. Solutions of collagen at various concentrations are prepared by reverse dialysis against polyethylene glycol (35 kDa, Fluka) dissolved in a 500 mM aqueous acetic acid solution, up to 50% (m/v), or by slow evaporation in a laminar flow hood. The collagen concentration of the acidic solution was determined before fibrillogenesis by determination of the amount of hydroxyproline. Of course, other collagen sources can be used.

EXAMPLE 1

A mineral phase precursor solution was prepared by dissolving, in 40 mL of water, 110 mM of NaH$_2$PO$_4$, 66 mM of CaCl$_2$, 500 mM of acetic acid and 0.40 µg of poly(aspartic acid). The solution is equilibrated at pH 2.2.

The collagen solution used in this example contained an amount of collagen of approximately 300 mg/mL. It is in the form of a partially fibrillar elastic gel.

The collagen solution was introduced into a dialysis bag (MW=3500 Da), and the bag was placed in the inorganic phase precursor solution in an open container. Said container was then placed under an ammonia atmosphere until complete precipitation of the salts at a temperature of 20° C.

The ammonia atmosphere caused a coprecipitation of collagen and hydroxyapatite, which was visible from 3 hours onward. The reaction medium can be left to mature for 8 days.

The samples were washed by immersion in a solution, advantageously a PBS phosphate buffered solution.

Figure 1:
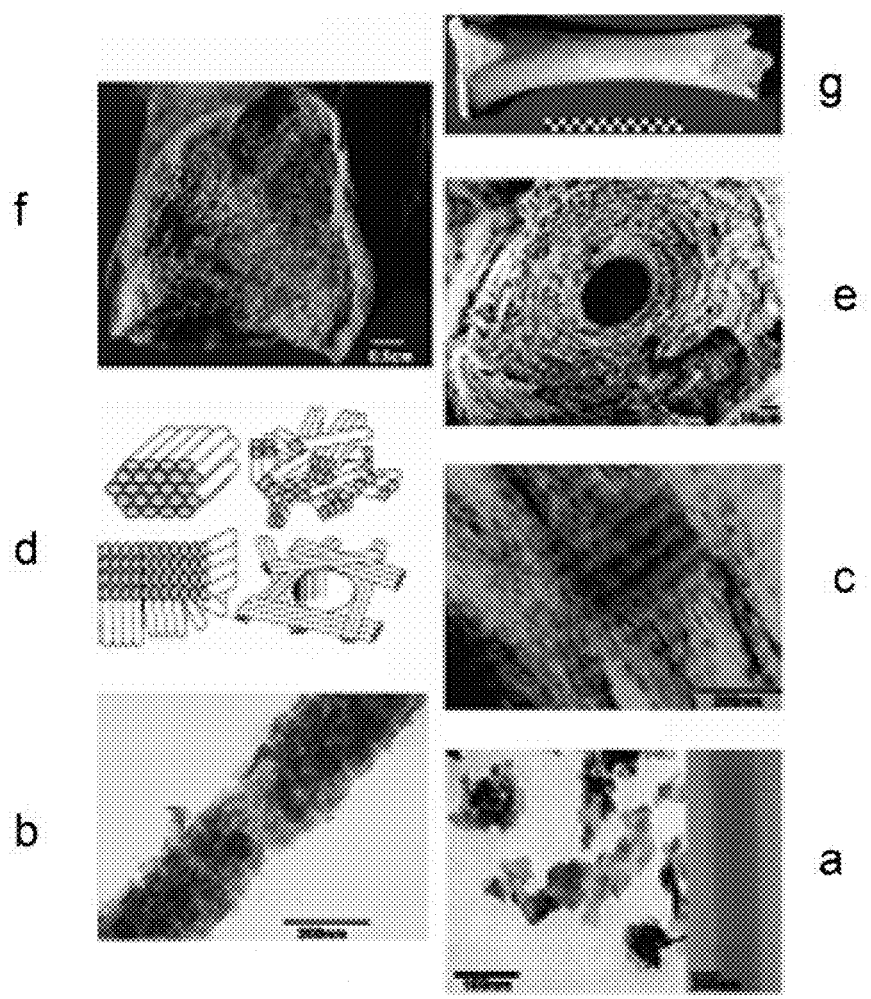
FIG. 1 shows a hierarchical organization of bone.
Figure 2:
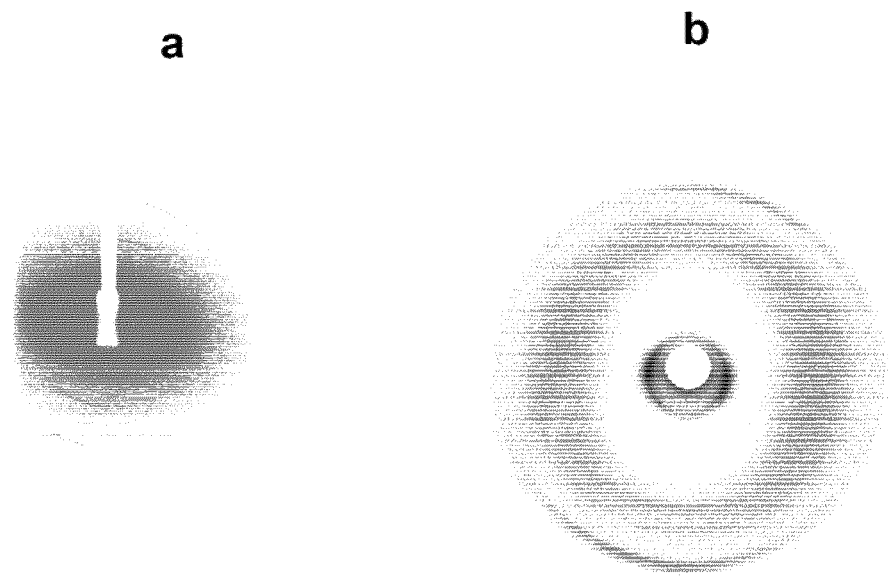
FIG. 2 is an X-ray scattering analysis of Example 1, in accordance with one embodiment.

FIG. 2 illustrates the analysis of the material by X-ray scattering. FIG. 2a represents an SAXS image and FIG. 2b represents a WAXS image. The SAXS to image shows the anisotropic signal of the collagen fibrils and the harmonics of the period D =67 nm; this demonstrates the periodicity of the striations every 67 nm along the main axis of the fibrils. The WAXS image shows that the (002) reflection, characteristic of the presence of apatite, is reinforced in the same direction as the fibril signal observed in (a). This therefore indicates that the c axis is of the apatite crystals is oriented along the main axis of the collagen fibrils. The signal corresponding to the interdistance $d_{lateral}$ of the collagen molecules in the fibril is perpendicular to the (002) reflection and parallel to the (300) reflection of the apatite. The inter-reticular planes are therefore preferentially oriented according to the direction of the collagen molecules. This X-ray scattering signature is comparable to that found on bone.

Figure 3:
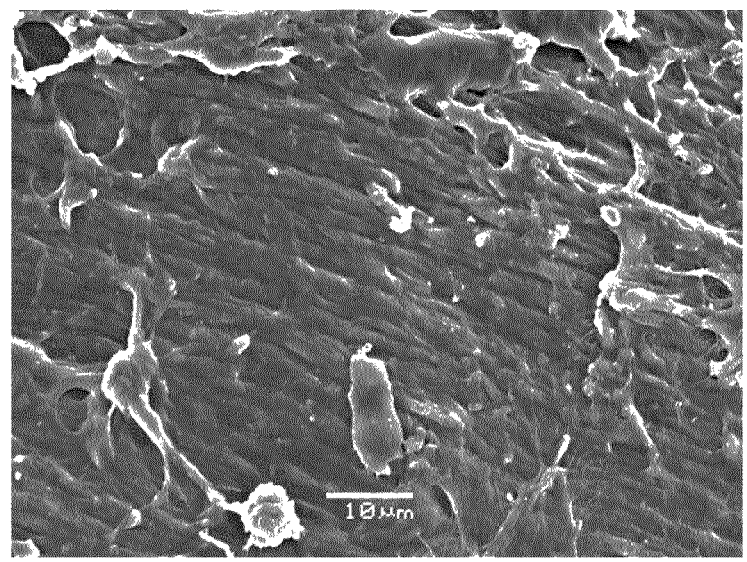
FIG. 3 is an SEM micrograph of Example 1, in accordance with one embodiment.

FIG. 3 represents an SEM micrograph. It shows the presence of mineralized oriented fibrils (aligned domains).

Figure 4:
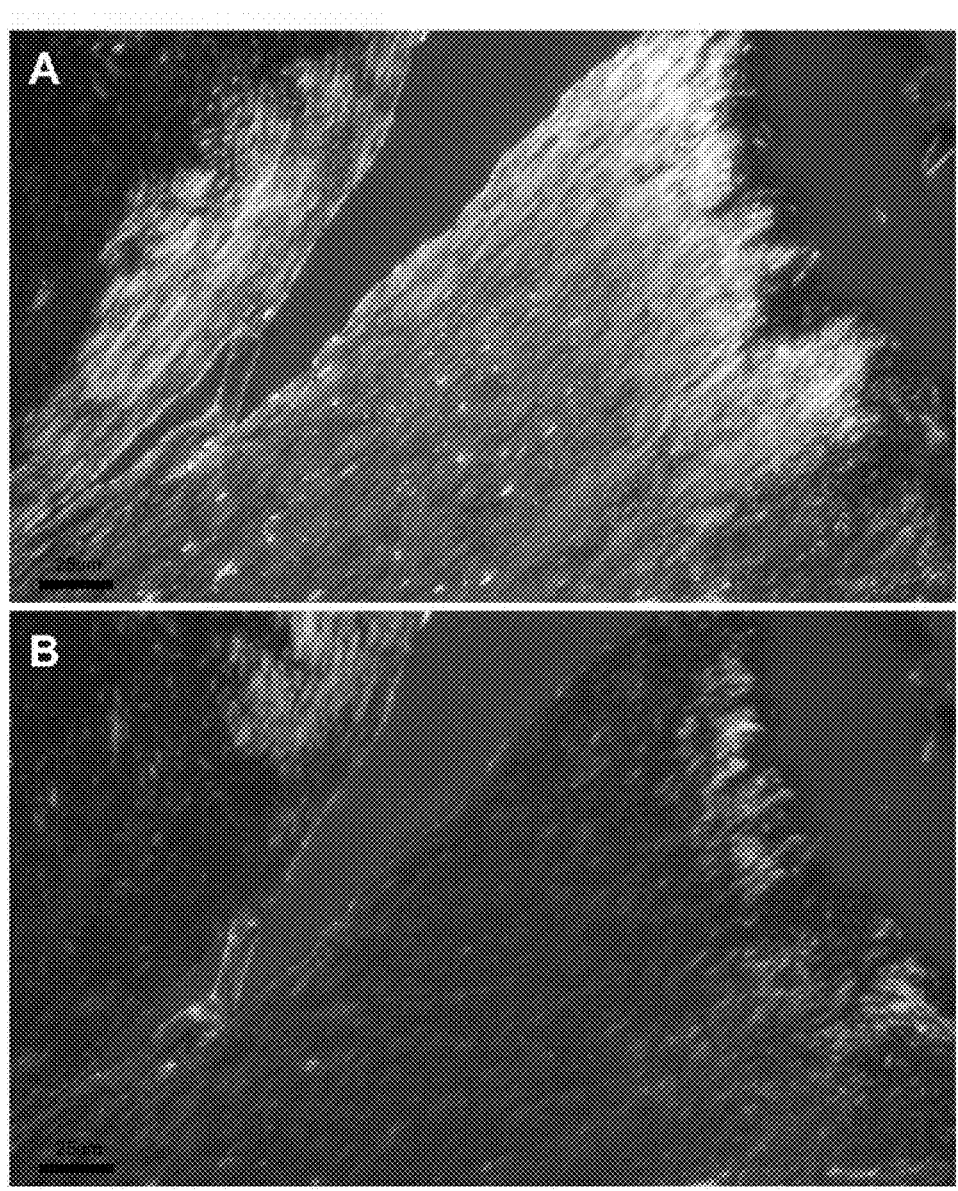
FIG. 4 is a semi-thin section of Example 1, in accordance with one embodiment.

FIG. 4 represents a semi-thin section stained with toluidine blue, which serves as a contrast agent for the material, observed by polarized-light optical microscopy between crossed polarizers (A,B). 4B represents the same zone as 4A, also observed between crossed polarizers but rotated 45° relative to 4A. The birefringence is due, on the one hand, to the organization of the organic phase and, on the other hand, to the impregnation thereof with the mineral phase. The variation in the birefringence bands between the two positions of the polarizers indicates the coexistence of distinct domains: (i) an aligned domain characterized by a zone of birefringence which is extinguished between 4A and 4B since the mineralized collagen fibrils are aligned with one another; and (ii) a cholesteric domain characterized by a zone of birefringence of which the alternating of light and dark bands inverts between 4A and 4B since the orientation of the mineralized collagen fibrils rotates regularly from one plane to the other. A third domain coexists with the previous two; this is an "isotropic" domain in which the mineralized collagen fibrils are randomly distributed in the material; this domain therefore exhibits no zone of birefringence in 4A and 4B.

Measurements of the mechanical properties of the material thus prepared were also carried out, in particular the elastic modulus, according to the nanoindentation technique. The measurements were carried out with a Ubi 1 nanomechanical indentation system (Hysitron Inc., Minneapolis, Minn., USA) and a Berkovich indenter tip, ~10 µm$^2$. It was found that the ratio of the elastic moduli at 0° and 90° relative to the longitudinal axis of the collagen fibrils is 1.43±1.18. The 10 order of magnitude of this ratio is comparable to that obtained for a native compact bone, i.e. 1.50±0.315, indicating that the degree of anisotropy of the present material, and thus its fibrillar organization, is similar to that found in bone.

EXAMPLE 2

A dilute solution of collagen (1 mg/L) was injected, in such a way as to counter water evaporation, into a 15 μL. glass microchamber. The injection was continued until a dense liquid crystalline collagen phase was obtained. The collagen was precipitated under an ammonia atmosphere, and the microchamber was then immersed in the solution of mineral precursors (said solution containing: 213.0 mM NaCl, 6.3 mM NaHCO$_3$, 4.5 mM KCl, 1.5 mM K$_2$HPO$_4$.3H$_2$O, 3.8 mM CaCl$_2$, 0.75 mM Na$_2$SO$_3$Na$_2$SO$_4$ and 2.3 mM MgCl$_2$.6K$_2$O) adjusted to pH 7.4 and kept in this solution for a period of 6 months at a temperature of 37° C.

The precipitated material was then washed by immersion in a phosphate buffered solution (PBS).

Figure 5:
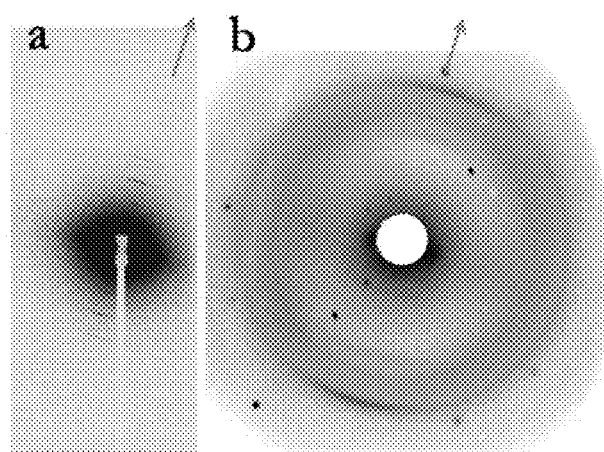
FIG. 5 is an X-ray scattering analysis of Example 2, in accordance with one embodiment.

FIG. 5 illustrates the analysis of the material by X-ray scattering. 5a represents an SAXS image and 5b represents a WARS image. The two images are analogous to those of example 1.

EXAMPLE 3

A collagen solution diluted to 5 mg/mL, previously dialyzed against a solution of NaH$_2$PO$_4$ (66 mM) and CaCl$_2$ (110 mM), was injected, in such a way as to counter water evaporation, into a 15 μL glass microchamber. The injection was continued until a dense liquid crystalline collagen phase was obtained. The microchamber was immersed in a solution of inorganic phase precursors that was analogous to that of example 1, in an open container. Said container was then placed under an ammonium carbonate atmosphere until complete precipitation of the salts at a temperature of 20° C.

The atmosphere of ammonia and carbon dioxide caused a coprecipitation of collagen and hydroxyapatite, which was visible from 3 hours onward. The reaction medium can be left to mature for 8 days.

The samples were washed by immersion in a phosphate buffered solution PBS.

Figure 6:
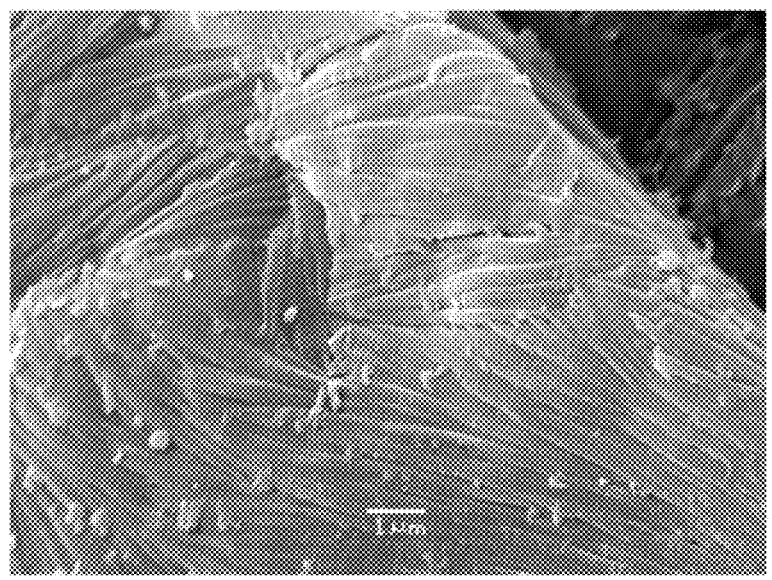
FIG. 6 is an SEM micrograph of Example 3, in accordance with one embodiment.

FIG. 6 represents an SEM micrograph. It shows the presence of mineralized fibers exhibiting a helicoidal organization (cholesteric domain).

The invention claimed is:

1. A synthetic material comprising:
    an organic phase (I); and
    a mineral phase (II), wherein
    the organic phase (I) comprises striated collagen fibrils constituted of collagen I triple helices and in which the periodicity of the striations is 67 nm, said fibrils being organized over a large distance according to a 3D geometry associating aligned domains and cholesteric domains, and also isotropic domains where they are not organized;
    the mineral phase (II) comprises apatite crystals having a hexagonal crystalline structure, space group 6/m, said crystals comprising at least calcium ions and at least phosphate ions;
    the axis c of the apatite crystals of the mineral phase is coaligned with the longitudinal axis of the striated collagen fibrils of the organic phase;
    the collagen content in said material is at least 75 mg/cm$^3$.

2. The material as claimed in claim 1, wherein the mineral phase consists of crystals of pure hydroxyapatite.

3. The material as claimed in claim 1, wherein the mineral phase consists of crystals of stoichiometric hydroxyapatite of formula (I) below:

$$Ca_{10}(PO_4)_6(OH)_2 \qquad (I).$$

4. The material as claimed in claim 3, wherein the Ca/P atomic ratio of the crystals of hydroxyapatite of formula (I) is 1.67.

5. The material as claimed in claim 1, wherein the mineral phase comprises apatite crystals also comprising at least hydroxide ions and in which the phosphate ions and/or the hydroxide ions are partially replaced with carbonate ions.

6. The material as claimed in claim 1, wherein the mineral phase comprises crystals of apatite comprising Ca$^{2+}$ ions, PO$_4^{3-}$ ions and OH$^-$ ions, and in which at least one of the Ca$^{2+}$, PO$_4^{3-}$ or OH$^-$ ions is partially replaced with other ions, it being understood that:
    the ions capable of partially replacing the Ca$^{2+}$ ions are selected from the group consisting of Mg$^{2+}$, Cu$^{2+}$, Sr$^{2+}$, Ba$^{2+}$, Zn$^{2+}$, Cd$^{2+}$, Pb$^{2+}$, Na$^+$, K$^+$ and Eu$^{3+}$ ions;
    the ions capable of partially replacing the PO$_4^{3-}$ ions are selected from the group consisting of CO$_3^{2-}$, SiO$_4^{3-}$, AsO$_4^{3-}$, MnO$_4^{3-}$, VO$_4^{3-}$, CrO$_4^{3-}$ and HPO$_4^{2-}$ions; and
    the ions capable of partially replacing the OH$^-$ ions are selected from the group consisting of CO$_3^{2-}$, F$^-$, Cl$^-$, Br$^-$, I$^-$, S$^{2-}$ and O$^{2-}$ ions.

7. The material as claimed in claim 1, wherein said material further comprises less than 2% of a compound selected from the group consisting of proteoglycans, glycosaminoglycans, organic molecules which promote mineralization and mixtures thereof.

* * * * *